US008093050B2

(12) United States Patent
Cho et al.

(10) Patent No.: US 8,093,050 B2
(45) Date of Patent: Jan. 10, 2012

(54) MTOR INHIBTORS AND MTOR SIGNALING PATHWAY INHIBITORS INDUCE DIFFERENTIATION OF HUMAN EMBRYONIC STEM CELLS INTO THE OSTEOBLASTIC LINEAGE

(75) Inventors: Yee Sook Cho, Daejeon (KR); Kyu-Won Lee, Chungnam (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 12/671,362

(22) PCT Filed: Aug. 17, 2007

(86) PCT No.: PCT/KR2007/003945
§ 371 (c)(1),
(2), (4) Date: Jul. 6, 2010

(87) PCT Pub. No.: WO2009/017269
PCT Pub. Date: Feb. 5, 2009

(65) Prior Publication Data
US 2010/0297755 A1    Nov. 25, 2010

(30) Foreign Application Priority Data

Aug. 1, 2007  (KR) .................. 10-2007-0077440

(51) Int. Cl.
*C12N 15/00* (2006.01)
(52) U.S. Cl. .................. 435/377; 435/366; 435/383
(58) Field of Classification Search .................. None
See application file for complete search history.

(56) References Cited

U.S. PATENT DOCUMENTS
2005/0282274 A1   12/2005   Xu et al.
2006/0173033 A1    8/2006   Kneissel et al.

FOREIGN PATENT DOCUMENTS
WO   WO 2006/020919 A2   2/2006
WO   WO 2006/027545 A2   3/2006

OTHER PUBLICATIONS

International Preliminary Report on Patentability, including the Written Opinion, for PCT/KR2007/003945, issued Feb. 2, 2010 by the International Bureau of WIPO, Geneva, Switzerland.
Ahn, S.E., et al., "Primary bone-derived cells induce osteogenic differentiation without exogenous factors in human embryonic stem cells," *Biochemical and Biophysical Research Communications* 340:403-408, Elsevier Inc., United Kingdom (Feb. 2006).
Barberi, T., et al., "Derivation of Multipotent Mesenchymal Precursors from Human Embryonic Stem Cells," *PLoS Medicine* 2(6):0554-0560, PLoS Medicine, United States (2005).
Bielby, R.C., et al., "In Vitro Differentiation and in Vivo Mineralization of Osteogenic Cells Derived from Human Embryonic Stem Cells," *Tissue Engineering* 10(9/10):1518-1525, Mary Ann Liebert, Inc., United States (2004).

Bonab, M.M., et al., "Aging of mesenchymal stem cell in vitro," *BMC Cell Biology* 7:14, BioMed Central, United Kingdom (Jan. 2006).
Buttery, L.D.K., et al., "Differentiation of Osteoblasts and in Vitro Bone Formation from Murine Embryonic Stem Cells," *Tissue Engineering* 7(1):89-99, Mary Ann Liebert, Inc., United States (2001).
Cao, T., et al., "Osteogenic differentiation within intact human embryoid bodies result in a marked increase in osteocalcin secretion after 12 days of in vitro culture, and formation of morphologically distinct nodule-like structures," *Tissue and Cell* 37:325-334, Elsevier, United Kingdom (2005).
Halleux, C.M., et al., "Secretion of Adiponectin and Regulation of apM1 Gene Expression in Human Visceral Adipose Tissue," *Biochemical and Biophysical Research Communications* 288:1102-1107, Academic Press, United States (2001).
Hashimoto, J., et al., "Regulation of Proliferation and Chondrogenic Differentiation of Human Mesenchymal Stem Cells by Laminin-5 (Laminin-332)," *Stem Cells* 24:2346-2354, AlphaMed Press, United States (Nov. 2006).
Hofmann, S.M., et al., "Adipocyte LDL receptor-related protein-1 expression modulates postprandial lipid transport and glucose homeostasis in mice," *J. Clin. Invest.* 117:3271-3282, American Society for Clinical Investigation, United States (Nov. 2007).
Jaiswal, N., et al., "Osteogenic Differentiation of Purified, Culture-Expanded Human Mesenchymal Stem Cells in Vitro," *Journal of Cellular Biochemistry* 64:295-312, Wiley-Liss., Inc., United States (1997).
Karp, J.M., et al., "Cultivation of Human Embryonic Stem Cells Without the Embryoid Body Step Enhances Osteogenesis in Vitro," *Stem Cells* 24:835-843, AlphaMed Press, United States (Apr. 2006).
Ogawa, T., et al., "Osteoblastic Differentiation Is Enhanced by Rapamycin in Rat Osteoblast-like Osteosarcoma (ROS 17/2.8) Cells," *Biochemical and Biophysical Research Communications* 249:226-230, Academic Press, United States (1998).
Schmelzle, T. and Hall, M.N., "TOR, a Central Controller of Cell Growth," *Cell* 103:253-262, Cell Press, United States (2000). Sottile, V., et al., "In Vitro Osteogenic Differentiation of Human ES Cells," *Cloning and Stem Cells* 5(2):149-155, Mary Ann Liebert, Inc., United States (2003).
Tang, L. et al., "FK506 Enhanced Osteoblastic Differentiation in Mesenchymal Cells," *Cell Biology International* 26(1):75-84, Academic Press, United States (2002).
Viñals, F., et al., "Inhibition of PI3K/p70 S6K and p38 MAPK cascades increases osteoblastic differentiation induced by BMP-2," *FEBS Letters* 510:99-104, Elsevier Science B.V., United Kingdom (2002).
Xin, X., et al., "Continuing differentiation of human mesenchymal stem cells and induced chondrogenic and osteogenic lineages in electrospun PLGA nanofiber scaffold," *Biomaterials* 28:316-325, Elsevier, United Kingdom (Jan. 2007).

*Primary Examiner* — Deborah Crouch
(74) *Attorney, Agent, or Firm* — Sterne, Kessler, Goldstein & Fox P.L.L.C.

(57) ABSTRACT

Disclosed are a composition for introducing the osteogenic differentiation of human embryonic stem cells and a method for differentiating human embryonic stem cells into an osteoblastic lineage by inhibiting the mTOR signaling pathway. When cultured in the presence of an inhibitor of the mTOR signaling pathway, human embryonic stem cells are effectively induced to differentiate into an osteoblastic lineage. The osteogenic differentiation of human embryonic stem cells using the method and the composition is useful in examining the development and differentiation mechanism of osteoblasts and the cause of metabolic bone diseases, including osteoporosis. In addition, the method and the composition can be applied to the development of osteogenic differentiation techniques for generating clinically useful, terminally differentiated mature cells or progenitor cells.

12 Claims, 12 Drawing Sheets

[FIG. 1]
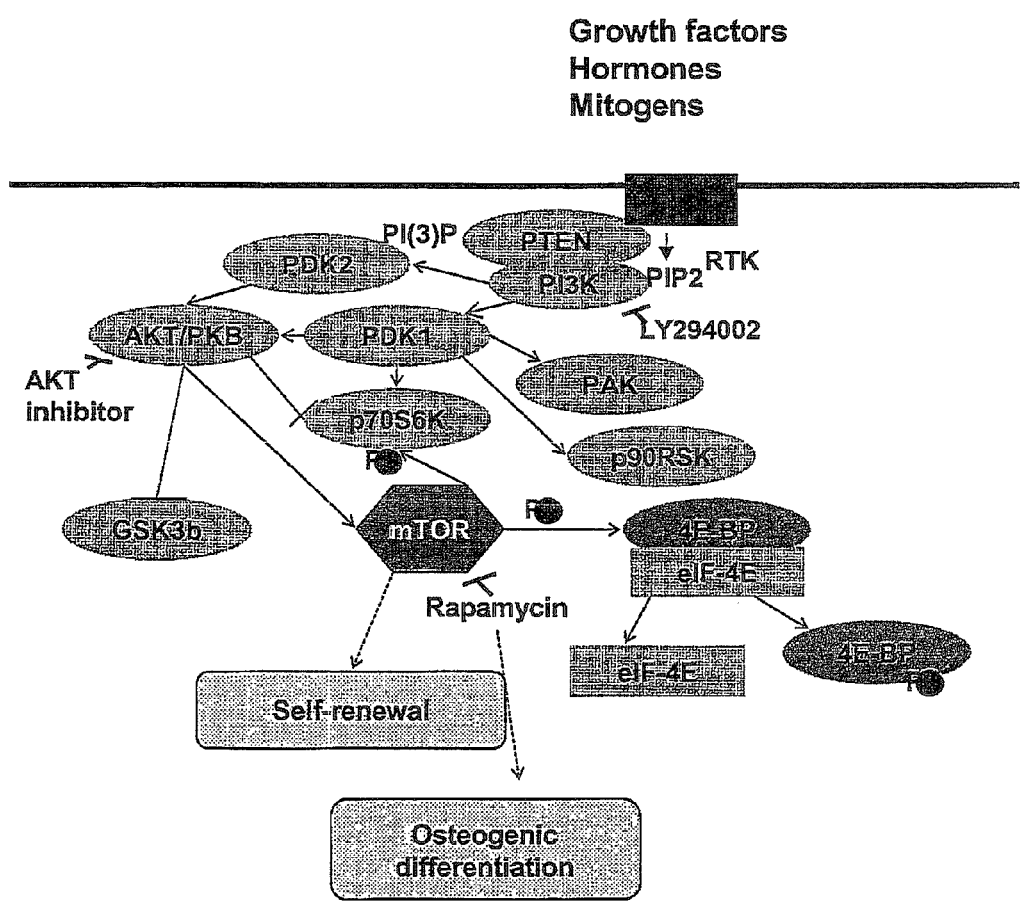

[FIG. 2]
A
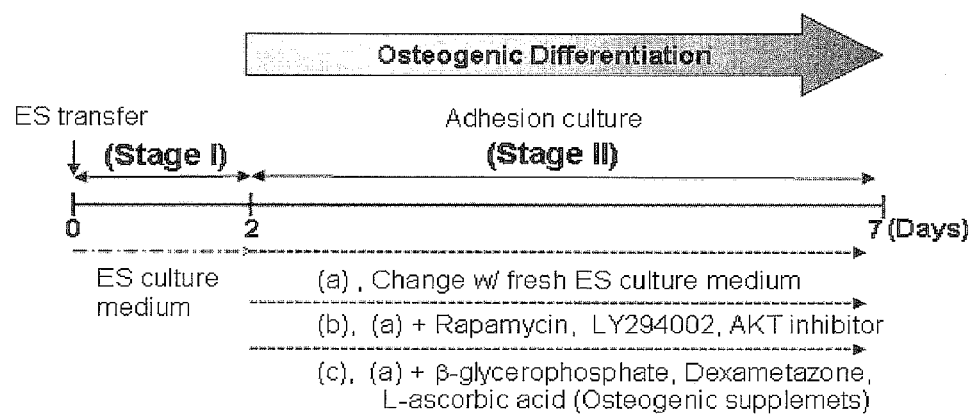
B
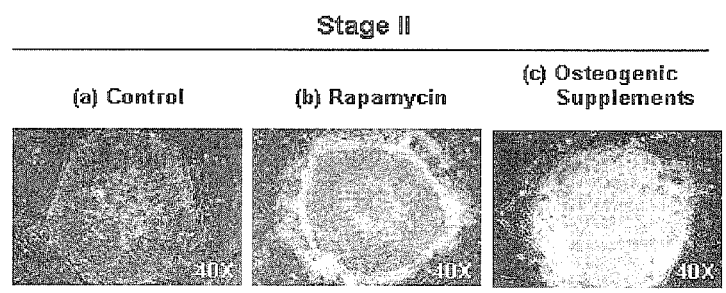

[FIG. 3]
A
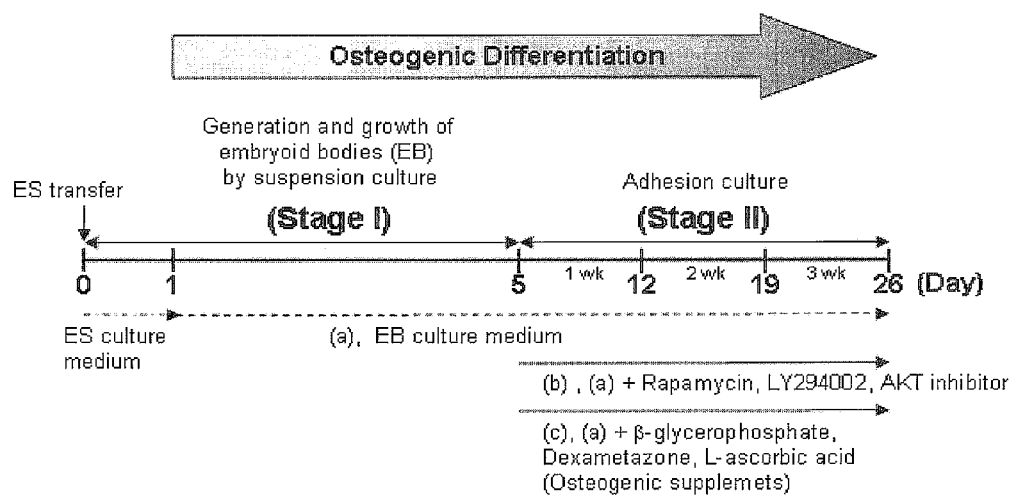
B
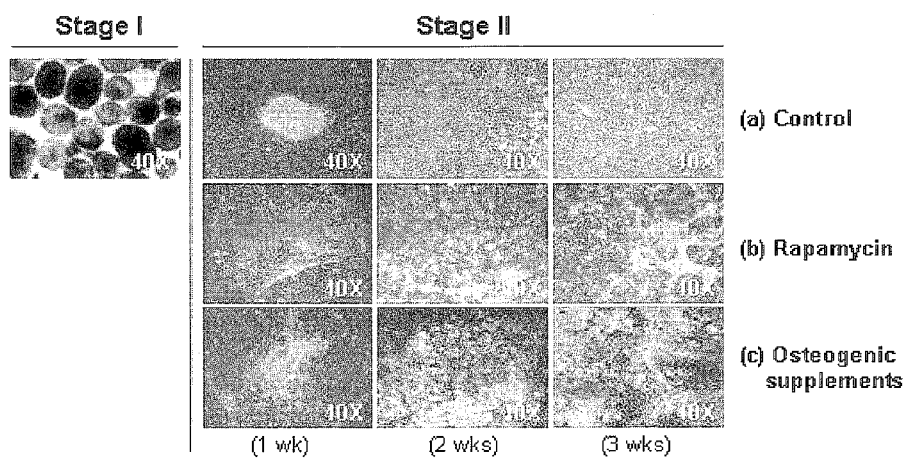

[FIG. 4]
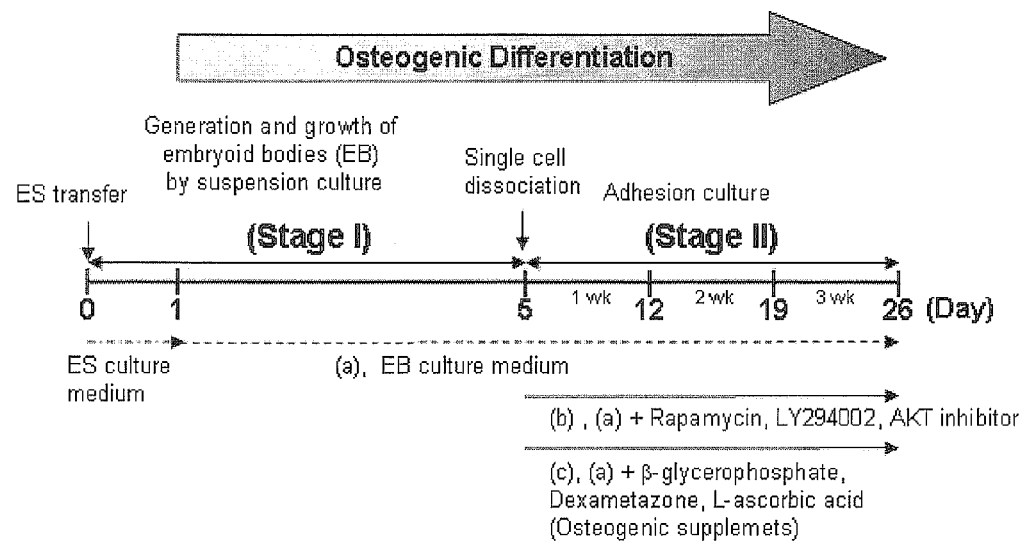
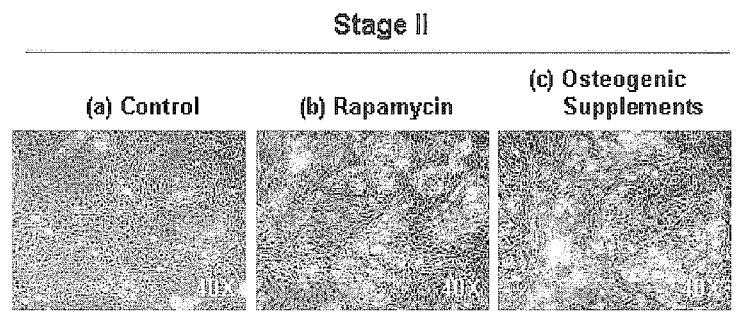

[FIG. 5]
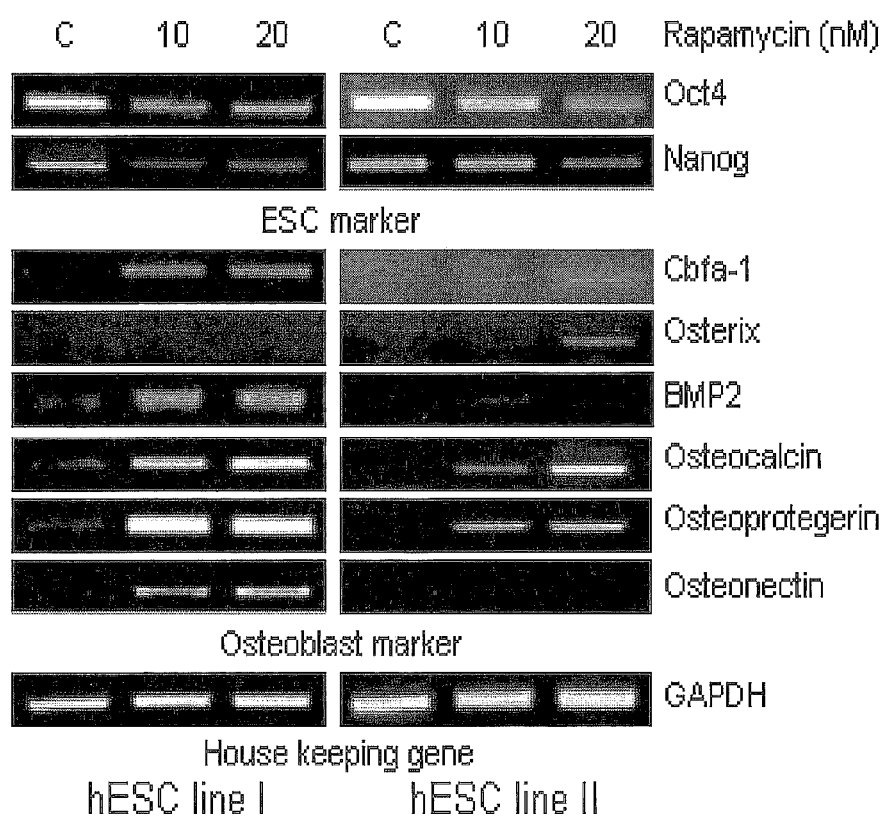

[FIG. 6]
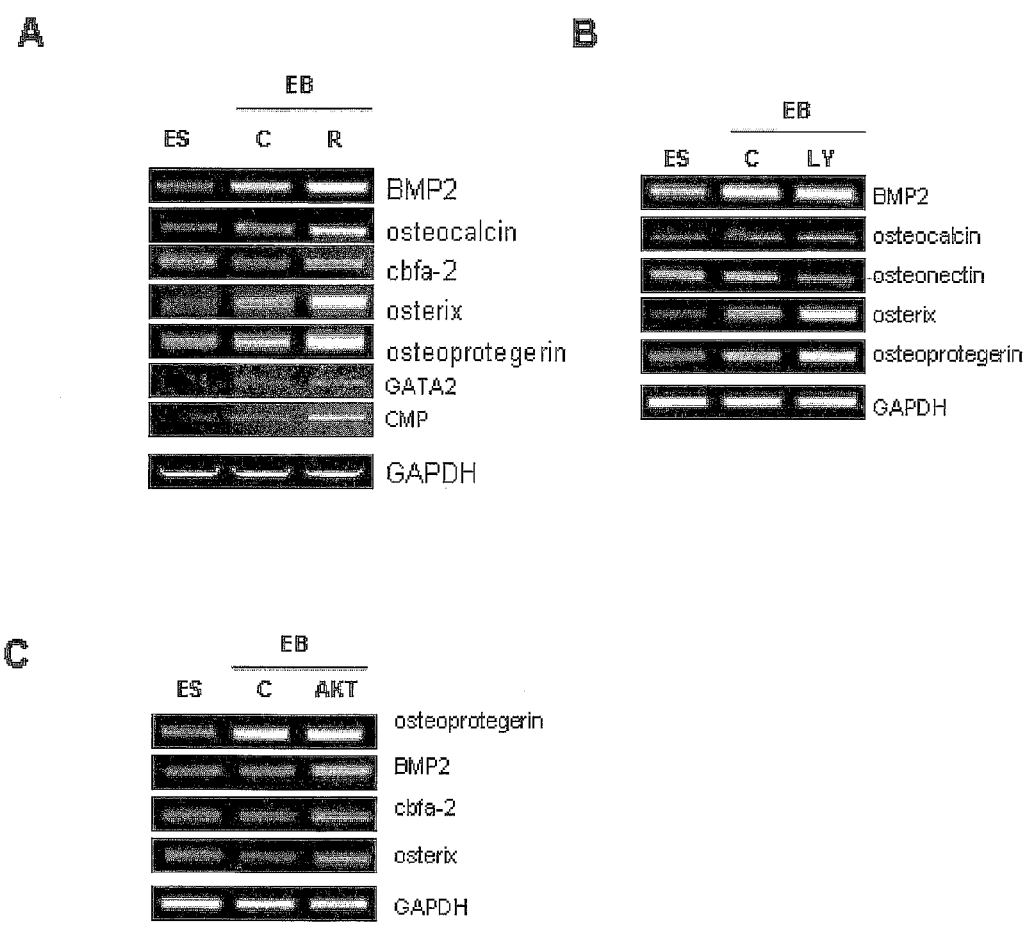

[FIG. 7]
A
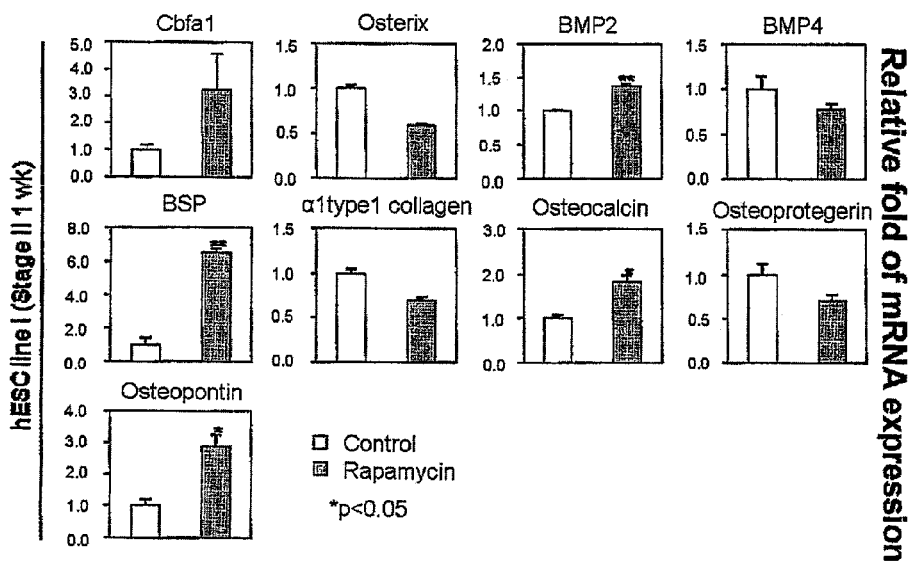
B
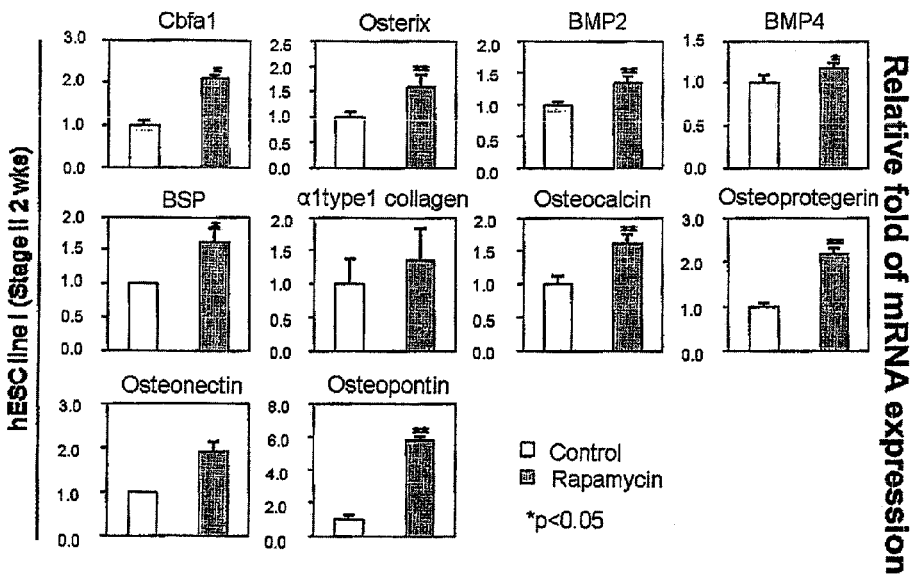

[FIG. 8]
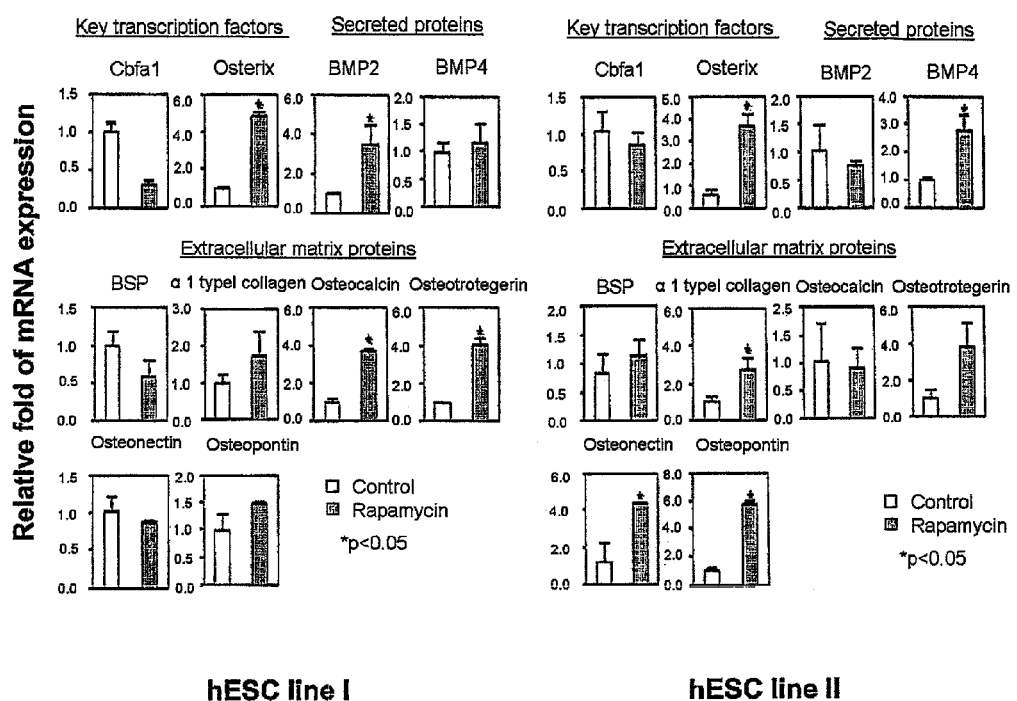

[FIG.9]
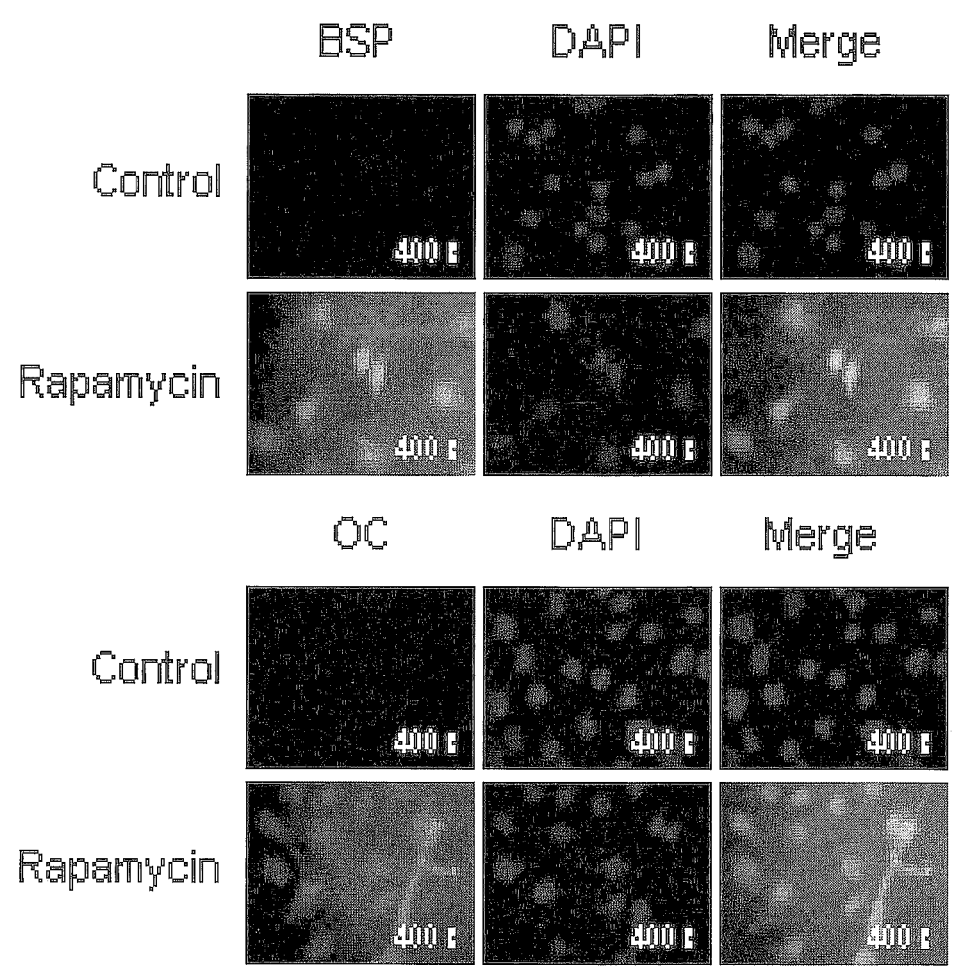

[FIG.10]
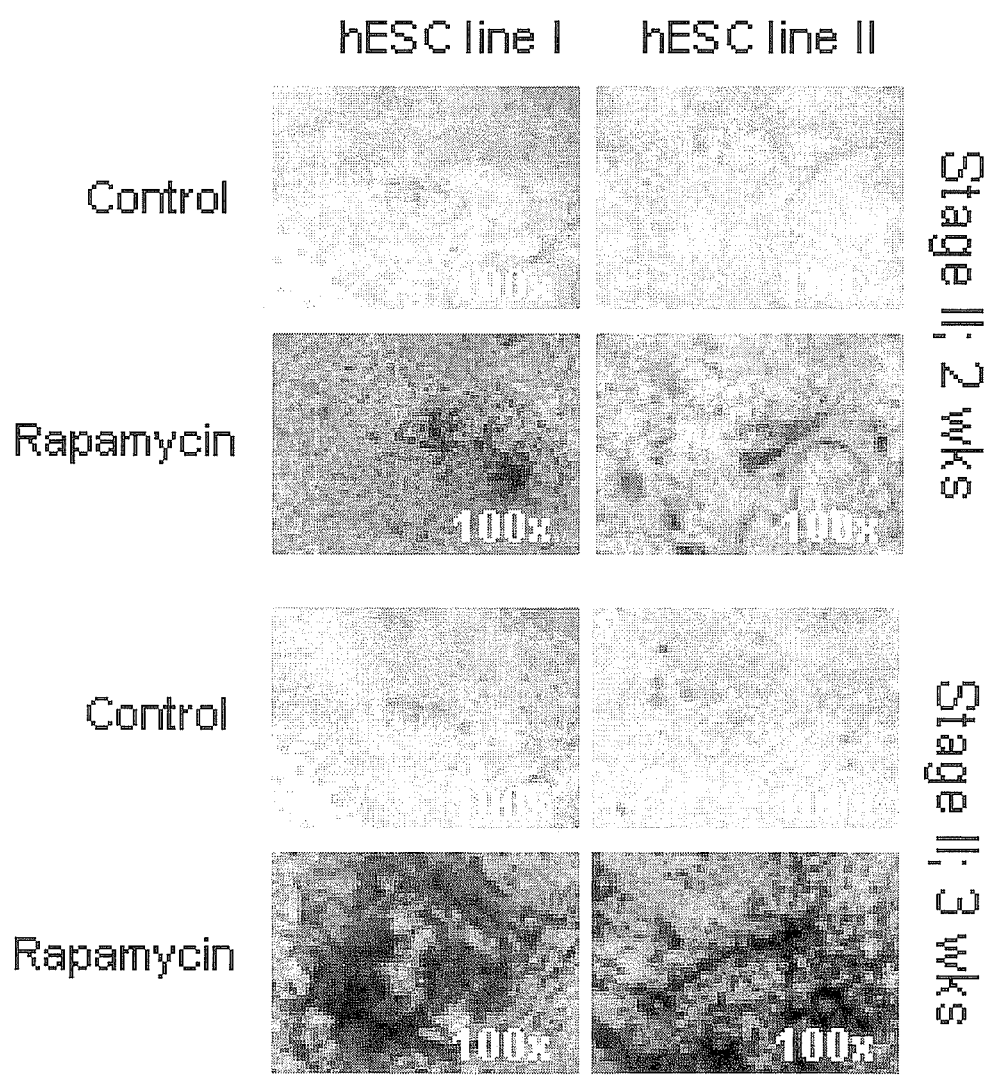

[FIG.11]
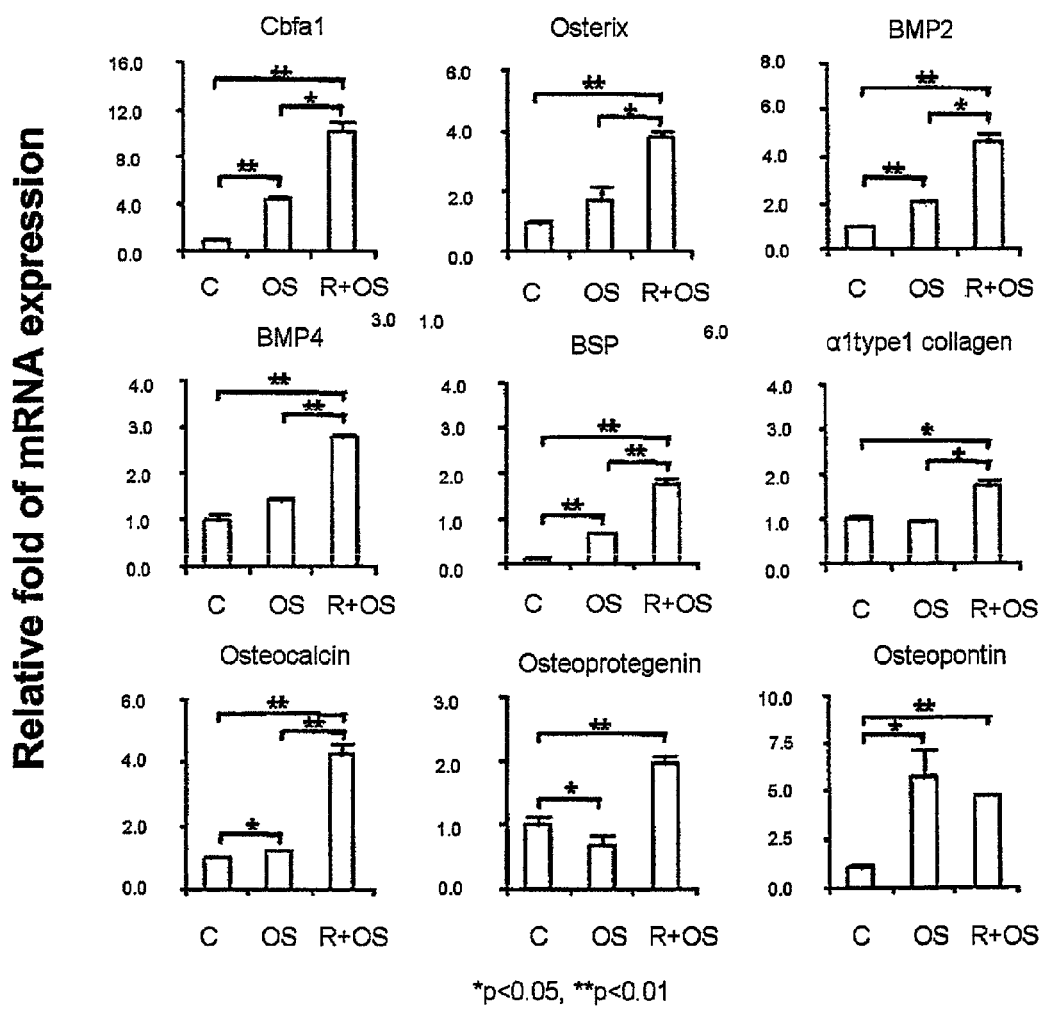

[FIG.12]
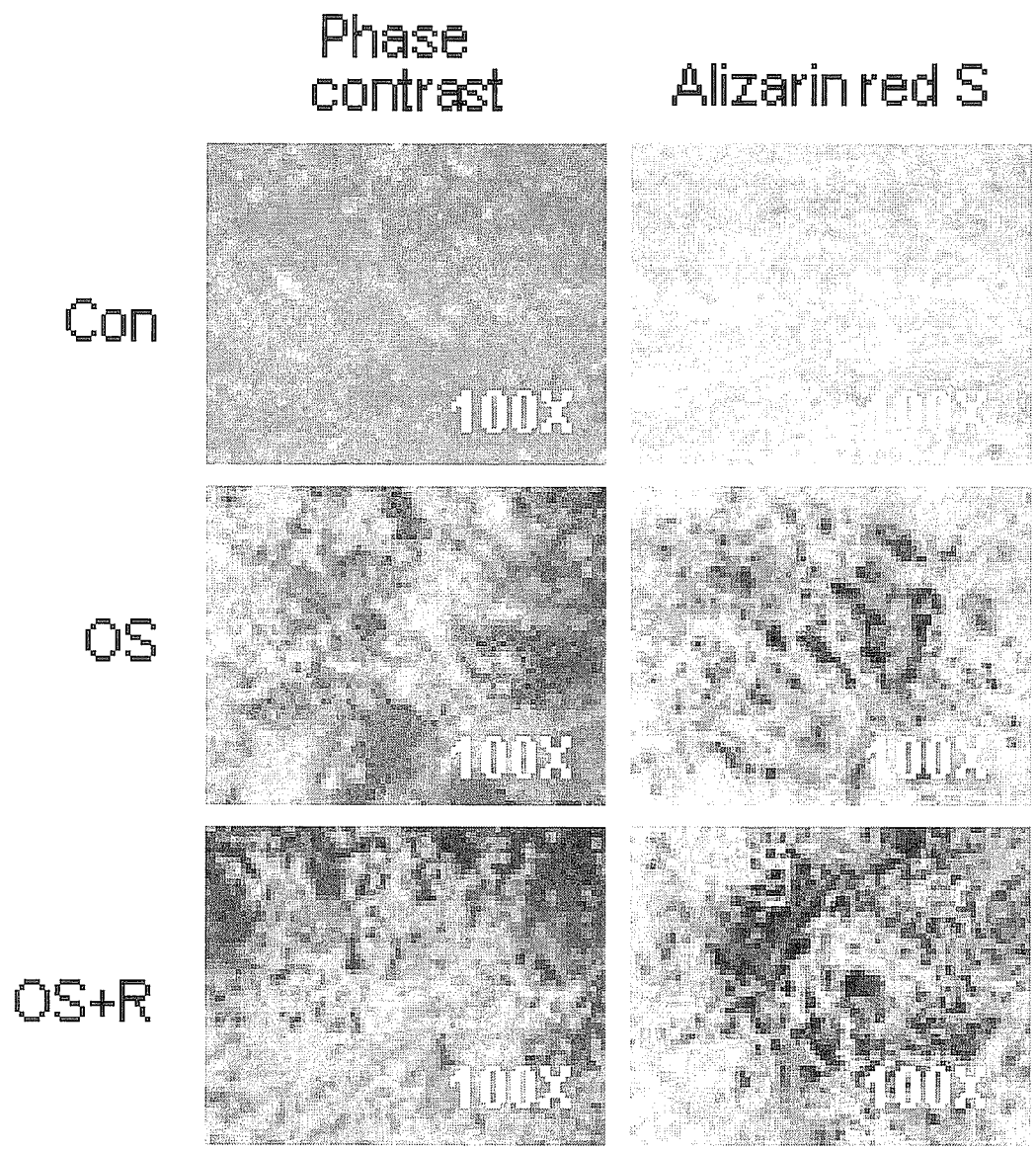

SEQUENCE LISTING

<160> NUMBER OF SEQ ID NOS: 34

<210> SEQ ID NO 1
<211> LENGTH: 19
<212> TYPE: DNA
<213> ORGANISM: Artificial Sequence
<220> FEATURE:
<223> OTHER INFORMATION: Forward primer for GAPDH

<400> SEQUENCE: 1
gaaggtgaag gtcggagtc                                                 19

<210> SEQ ID NO 2
<211> LENGTH: 20
<212> TYPE: DNA
<213> ORGANISM: Artificial Sequence
<220> FEATURE:
<223> OTHER INFORMATION: Reverse primer for GAPDH

<400> SEQUENCE: 2
gaagatggtg atgggatttc                                                20

<210> SEQ ID NO 3
<211> LENGTH: 20
<212> TYPE: DNA
<213> ORGANISM: Artificial Sequence
<220> FEATURE:
<223> OTHER INFORMATION: Forward primer for Oct4

<400> SEQUENCE: 3
gaaggatgtg gtccgagtgt                                                20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for Oct4

<400> SEQUENCE: 4
gtgacagaga caggggggaaa                                               20

<210> SEQ ID NO 5
<211> LENGTH: 24
<212> TYPE: DNA
<213> ORGANISM: Artificial Sequence

```
<220> FEATURE:
<223> OTHER INFORMATION: Forward primer for Nanog

<400> SEQUENCE: 5
accagaactg tgttctcttc cacc                                           24

<210> SEQ ID NO 6
<211> LENGTH: 24
<212> TYPE: DNA
<213> ORGANISM: Artificial Sequence
<220> FEATURE:
<223> OTHER INFORMATION: Reverse primer for Nanog

<400> SEQUENCE: 6
ggttgctcca ggttgaattg ttcc                                           24

<210> SEQ ID NO 7
<211> LENGTH: 20
<212> TYPE: DNA
<213> ORGANISM: Artificial Sequence
<220> FEATURE:
<223> OTHER INFORMATION: Forward primer for ALP

<400> SEQUENCE: 7
gggggtggcc ggaaatacat                                                20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for ALP

<400> SEQUENCE: 8
gggggccaga ccaaagatag                                                20

<210> SEQ ID NO 9
<211> LENGTH: 21
<212> TYPE: DNA
<213> ORGANISM: Artificial Sequence
<220> FEATURE:
<223> OTHER INFORMATION: Forward primer fof ALP asterisk

<400> SEQUENCE: 9
ccgtggcaac tctatctttg g                                              21

<210> SEQ ID NO 10
<211> LENGTH: 21
<212> TYPE: DNA
<213> ORGANISM: Artificial Sequence
<220> FEATURE:
<223> OTHER INFORMATION: Reverse primer for ALP asterisk

<400> SEQUENCE: 10
gatggcagtg aagggcttct t                                              21

<210> SEQ ID NO 11
<211> LENGTH: 23
<212> TYPE: DNA
<213> ORGANISM: Artificial Sequence
<220> FEATURE:
<223> OTHER INFORMATION: Forward primer for alpha1 type I collagen

<400> SEQUENCE: 11
atggattcca gttcgagtat ggc                                            23
```

-continued

<210> SEQ ID NO 12
<211> LENGTH: 21
<212> TYPE: DNA
<213> ORGANISM: Artificial Sequence
<220> FEATURE:
<223> OTHER INFORMATION: Reverse primer alpha1 type I collagen

<400> SEQUENCE: 12
catcgacagt gacgctgtag g                                              21

<210> SEQ ID NO 13
<211> LENGTH: 19
<212> TYPE: DNA
<213> ORGANISM: Artificial Sequence
<220> FEATURE:
<223> OTHER INFORMATION: Forward primer for BMP2

<400> SEQUENCE: 13
acccgctgtc ttctagcgt                                                 19

<210> SEQ ID NO 14
<211> LENGTH: 20
<212> TYPE: DNA
<213> ORGANISM: Artificial Sequence
<220> FEATURE:
<223> OTHER INFORMATION: Reverse primer for BMP2

<400> SEQUENCE: 14
ctcaggacct cgtcagaggg                                                20

<210> SEQ ID NO 15
<211> LENGTH: 21
<212> TYPE: DNA
<213> ORGANISM: Artificial Sequence
<220> FEATURE:
<223> OTHER INFORMATION: Forward primer for BMP4

<400> SEQUENCE: 15
tgttcaccgt tttctcgact c                                              21

<210> SEQ ID NO 16
<211> LENGTH: 21
<212> TYPE: DNA
<213> ORGANISM: Artificial Sequence
<220> FEATURE:
<223> OTHER INFORMATION: Reverse primer for BMP4

<400> SEQUENCE: 16
tcaggtatca aactagcatg g                                              21

<210> SEQ ID NO 17
<211> LENGTH: 19
<212> TYPE: DNA
<213> ORGANISM: Artificial Sequence
<220> FEATURE:
<223> OTHER INFORMATION: Forward primer for BSP

<400> SEQUENCE: 17
cagtatgact catccgaag                                                 19

<210> SEQ ID NO 18
<211> LENGTH: 20
<212> TYPE: DNA
<213> ORGANISM: Artificial Sequence
<220> FEATURE:
<223> OTHER INFORMATION: Reverse primer for BSP

<400> SEQUENCE: 18
ctcctcttct tcttcatcac                                              20

<210> SEQ ID NO 19
<211> LENGTH: 23
<212> TYPE: DNA
<213> ORGANISM: Artificial Sequence
<220> FEATURE:
<223> OTHER INFORMATION: Forward primer for BSP asterisk

<400> SEQUENCE: 19
agaggaagca atcaccaaaa tga                                          23

<210> SEQ ID NO 20
<211> LENGTH: 18
<212> TYPE: DNA
<213> ORGANISM: Artificial Sequence
<220> FEATURE:
<223> OTHER INFORMATION: Reverse primer for BSP asterisk

<400> SEQUENCE: 20
gcacaggcca ttcccaaa                                                18

<210> SEQ ID NO 21
<211> LENGTH: 19
<212> TYPE: DNA
<213> ORGANISM: Artificial Sequence
<220> FEATURE:
<223> OTHER INFORMATION: Forward primer for Cbfa1

<400> SEQUENCE: 21
cggcaaaatg agcgacgtg                                               19

<210> SEQ ID NO 22
<211> LENGTH: 19
<212> TYPE: DNA
<213> ORGANISM: Artificial Sequence
<220> FEATURE:
<223> OTHER INFORMATION: Reverse primer for Cbfa1

<400> SEQUENCE: 22
caccgagcac aggaagttg                                               19

<210> SEQ ID NO 23
<211> LENGTH: 19
<212> TYPE: DNA
<213> ORGANISM: Artificial Sequence
<220> FEATURE:
<223> OTHER INFORMATION: Forward primer for Osteocalcin

<400> SEQUENCE: 23
cactcctcgc cctattggc                                               19

<210> SEQ ID NO 24
<211> LENGTH: 21
<212> TYPE: DNA
<213> ORGANISM: Artificial Sequence
<220> FEATURE:
<223> OTHER INFORMATION: Reverse primer for Osteocalcin

<400> SEQUENCE: 24
gcctgggtct cttcactacc t                                            21

<210> SEQ ID NO 25
<211> LENGTH: 19
<212> TYPE: DNA
<213> ORGANISM: Artificial Sequence

```
<220> FEATURE:
<223> OTHER INFORMATION: Forward primer for Osteonectin

<400> SEQUENCE: 25
agcaccccat tgacgggta                                              19

<210> SEQ ID NO 26
<211> LENGTH: 21
<212> TYPE: DNA
<213> ORGANISM: Artificial Sequence
<220> FEATURE:
<223> OTHER INFORMATION: Reverse primer for Osteonectin

<400> SEQUENCE: 26
ggtcacaggt ctcgaaaaag c                                           21

<210> SEQ ID NO 27
<211> LENGTH: 22
<212> TYPE: DNA
<213> ORGANISM: Artificial Sequence
<220> FEATURE:
<223> OTHER INFORMATION: Forward primer for Osteopontin

<400> SEQUENCE: 27
actcgaacga ctctgatgat gt                                          22

<210> SEQ ID NO 28
<211> LENGTH: 22
<212> TYPE: DNA
<213> ORGANISM: Artificial Sequence
<220> FEATURE:
<223> OTHER INFORMATION: Reverse primer for Osteopontin

<400> SEQUENCE: 28
gtcaggtctg cgaaacttct ta                                          22

<210> SEQ ID NO 29
<211> LENGTH: 21
<212> TYPE: DNA
<213> ORGANISM: Artificial Sequence
<220> FEATURE:
<223> OTHER INFORMATION: Forward primer for Osteoprotegerin

<400> SEQUENCE: 29
agcaccctgt agaaaacaca c                                           21

<210> SEQ ID NO 30
<211> LENGTH: 22
<212> TYPE: DNA
<213> ORGANISM: Artificial Sequence
<220> FEATURE:
<223> OTHER INFORMATION: Reverse primer for Osteoprotegerin

<400> SEQUENCE: 30
acactaagcc agttaggcgt aa                                          22

<210> SEQ ID NO 31
<211> LENGTH: 20
<212> TYPE: DNA
<213> ORGANISM: Artificial Sequence
<220> FEATURE:
<223> OTHER INFORMATION: Forward primer for Osterix

<400> SEQUENCE: 31
cccaggcaac actcctactc                                             20
```

```
<210> SEQ ID NO 32
<211> LENGTH: 21
<212> TYPE: DNA
<213> ORGANISM: Artificial Sequence
<220> FEATURE:
<223> OTHER INFORMATION: Reverse primer for Osterix

<400> SEQUENCE: 32
ggctggatta aggggagcaa a                                          21

<210> SEQ ID NO 33
<211> LENGTH: 20
<212> TYPE: DNA
<213> ORGANISM: Artificial Sequence
<220> FEATURE:
<223> OTHER INFORMATION: Forward primer for Osterix asterisk

<400> SEQUENCE: 33
gctctgctcc aagcgcttta                                            20

<210> SEQ ID NO 34
<211> LENGTH: 18
<212> TYPE: DNA
<213> ORGANISM: Artificial Sequence
<220> FEATURE:
<223> OTHER INFORMATION: Reverse primer for Osterix asterisk

<400> SEQUENCE: 34
ggtgcgctgg tgtttgct                                              18
```

MTOR INHIBTORS AND MTOR SIGNALING PATHWAY INHIBITORS INDUCE DIFFERENTIATION OF HUMAN EMBRYONIC STEM CELLS INTO THE OSTEOBLASTIC LINEAGE

CROSS REFERENCE TO RELATED APPLICATIONS

This application is the National Stage of International Application No. PCT/KR2007/003945, filed Aug. 17, 2007, which claims priority to Korean Application No. 10-2007-0077440, filed Aug. 1, 2007.

REFERENCE TO SEQUENCE LISTING SUBMITTED ELECTRONICALLY VIA EFS-WEB

The content of the electronically submitted sequence listing (Name: SeqList.txt Size: 7,772 bytes; and Date of Creation: Jun. 30, 2010) filed herewith is incorporated herein by reference in its entirety.

TECHNICAL FIELD

The present invention relates to a method for differentiating human embryonic stem cells into an osteoblastic lineage, using an inhibitor against the mTOR signaling pathway, and a composition for inducing osteogenic differentiation.

BACKGROUND ART

Stem cells, especially human embryonic stem cells, have recently arisen as a promising cell therapeutic in the regenerative medicine and medical industries. In recognition of the economic and industrial use and added value of human embryonic stem cells, the development of technologies and materials for inducing human embryonic stem cells to differentiate into functionally specific cells has emerged as one of the most interesting topics. As embryonic stem cells were first derived from mouse embryos in 1981 by Evans and Kaufman, mouse embryonic stem cells have been used as basic materials for use in the study of embryonic stem cells and the development of differentiation inducing technologies.

Embryonic stem cells possess two characteristic properties: self-renewal—the ability to go through numerous cycles of cell division under ex vivo conditions without differentiation while maintaining a normal nucleus type; and potency—the capacity to differentiate, at least theoretically, into almost all specialized cell types that constitute the body under culture conditions. These surprising properties greatly require technologies and materials for the development and application of human embryonic stem cells. Since 1998, when a breakthrough in human embryonic stem cell research came when Thomson first developed a technique for isolating and growing cells when derived from the inner cell mass of human blastocysts, active research has been conducted to develop technologies targeting human embryonic stem cells, especially technologies for tissue-specific differentiation-inducing technologies. Many research reports disclose successes in the differentiation of human embryonic stem cells into retinal progenitor cells (Lamba D A et al., 2006), nerve cells (Li X J et al., 2006; Zhang S C et al., 2001), hematopoietic cells (Tian X et al., 2005; Kaufman D S et al., 2005; Kaufman D S et al., 2001), cardiomuscular cells (Kehat I et al., 2003; Kehat I et al., 2001), and pancreatic cells (Assady S et al., 2001) under ex vivo culture conditions, and the possibility of using human embryonic stem cells as cell therapeutics was also suggested (Zhang S C et al., 2001).

The bone maintains the homeostasis thereof through bone formation and remodeling. The site at which active bone remodeling takes place is known as a bone remodeling unit (BRU) or bone multicellular unit, which consists of osteoblasts and osteoclasts, which play critical roles in osteogenesis and bone resorption, respectively. A hindrance to cooperation between the two cells in the remodeling process gives rise to various metabolic bone diseases, including osteoporosis. However, none of the therapies developed thus far ensure complete recovery from metabolic bone diseases. Thus, there is still emphasis on the prophylaxis of metabolic bone diseases in the medical field.

Extensive efforts have recently been made to produce osteoblasts using stem cell differentiation inducing techniques and to apply osteoblasts to the enhancement of bone tissue functions and the treatment of bone tissue injuries. As osteoblasts responsible for bone formation are naturally derived from mesenchymal stem cells (Caplan A I, 1991), immense attention has been paid to the use of mesenchymal stem cells in inducing osteogenic differentiation and as cell therapeutics (Halleux C at al., 2001; Jaiswal N et al., 1997; Hashimoto J et al., 2006; Hofmann S et al., 2007; Xin X et al., 2007; Quarto R et al., 2001). The mesenchymal stem cells of adult tissues may be a useful approach to bone regeneration with autogenous bone grafts, but are disadvantageous in that they are very small in number and difficult to collect by bone marrow aspiration. Hence, the collected cells must be proliferated to a necessary population by ex vivo culturing. However, the fact that a limitation on the possible number of cell division cycles exists and that there is a high possibility of inducing cell modification during the large number of cycles of cell division act as a bottleneck for the use of mesenchymal stem cells. It was reported that nine or more passages cause mesenchymal stem cells to experience aging and lose stem cell properties and osteogenetic potency (Bonab M M et al., 2006). On the other hand, early-stage human embryonic stem cells enjoy the advantage of being applicable to the treatment of various diseases not only because they are a means of understanding the mechanism of osteogenic differentiation, but also because a relatively large number of the cells can be supplied thanks to the ability thereof to proliferate through numerous cycles of cell division under ex vivo culture conditions.

Osteogenic supplements, such as ascorbic acid, β-glycerophosphate, and dexamethasone, are reported to be useful in the induction of osteogenic differentiation (Karp J M et al., 2006; Cao T et al., 2005; Bielby R C et al., 2004; Sottile V et al., 2003). Also reported are induction methods for the differentiation of human embryonic stem cells into osteoblasts by co-culturing with cells derived from bone tissues (Ahn S E et al., 2006), and the differentiation of human embryonic stem cell-derived mesenchymal stem cells into osteoblasts (Barberi T et al., 2005; US2005/0282274 A1). The transforming growth factor-beta (TGF-beta) subfamily, including activin, bone morphogenetic protein (BMP), inhibin, and growth/differentiation factor (GDF), is known to play a critical role in the formation and maintenance of bone tissues. Particularly, human embryonic stem cells are potentially induced to differentiate into osteoblasts when cultured in the presence of BMP2 or BMP4. The understanding of the mechanism by which osteoblasts are differentiated from embryonic stem cells and the techniques of inducing the differentiation have not advanced to a level sufficient to develop cell therapeutics having excellent clinical functions. In order to overcome this, it is important to understand factors involved in osteoblast differentiation and their mechanisms. It is also important to find materials controlling the differentiation factors and utilize them in the induction of osteoblast differentiation.

mTOR (mammalian target of rapamycin), a member of the PIKK (phosphoinositide kinase-related kinase) family, is an important downstream mediator in the PI3k/Akt signaling pathway, which is known to play a critical role in controlling the proliferation and differentiation of embryonic stem cells. Rapamycin binds intracellularly to FK506 binding protein-12 (FKBP12) and the rapamycin-FKBP12 complex targets mTOR, inhibiting its kinase activity, which in turn inhibits the phosphorylation and activation of the downstream translational regulators p70S6 kinase 1 (S6K1) and eukaryotic initiation factor 4E (eIF4E) binding protein 1 (4E-BP1). By phosphorylation, mTOR activates the downstream translational regulators, thus promoting various intracellular functions including protein synthesis (Harris T E et al., 2003). Rapamycin, known as an immunosuppressive, is reported to have the activity of inducing the differentiation of various cell lines including mesenchymal stem cells into osteoblasts (Ogawa T et al., 1998; Tang L et al., 2002), and to have a therapeutic effect on osteolysis (US2006/0173033 A1). Also, recent findings suggest that phosphatidic acid, a competitor with rapamycin, activates mTOR, increasing the self-renewal of stem cells while 1-butanol and rapamycin, identified as antagonists of mTOR, inhibit mTOR activity, inducing the differentiation of stem cells (WO 2006/027545 A2, A3).

Many studies on human embryonic stem cells are conducted on the basis of results of research on mouse embryonic stem cells, but it is reported that there are differences between human and mouse embryonic stem cells in proliferation and differentiation properties and relevant molecular regulation mechanisms. Intensive and thorough research into the differentiation of human embryonic stem cells, conducted by the present inventors, resulted in the finding that human embryonic stem cells are induced to effectively differentiate into an osteoblastic lineage in a culture medium supplemented with an inhibitor against mTOR, known to play an important role in a cellular signaling pathway, leading to the present invention.

DISCLOSURE

Technical Problem

It is therefore an object of the present invention to provide a composition for inducing the differentiation of human embryonic stem cells into an osteoblastic lineage.

It is another object of the present invention to provide a method for inducing the differentiation of human embryonic stem cells into an osteoblastic lineage by culturing the cells in a culture medium comprising the composition.

Technical Solution

In order to accomplish the above objects, the present invention provides a composition for inducing the differentiation of human embryonic stem cells into an osteoblastic lineage, comprising an inhibitor of mTOR, which inhibits the signal transmission in which mTOR is involved, in accordance with an aspect of the present invention. Preferably, the inhibitor of mTOR functions downstream or upstream of the mTOR signaling pathway, and is selected from among rapamycin, a PI3K inhibitor, an AKT inhibitor, and combinations thereof.

mTOR (mammalian target of Rapamycin), also named FKBP12 rapamycin-associated protein (FRAP/RAFT/RAPT/SEP), is a serine/threonine protein kinase, which is an evolutionarily conserved member of phosphoinositol kinase-related kinase (PIKK). mTOR is involved in the regulation of cell growth through the initiation of gene translation in response to nutrients such as amino acids (mainly leucine), growth factors, insulin and mitogens. mTOR initiates translation by activating the ribosomal p70S6k protein kinase (S6K1) and by inhibiting the eIF4E inhibitor 4E-BP1. mTOR is thought to be involved in numerous additional cellular functions including actin organization, membrane trafficking secretion, protein degradation, protein kinase C signaling, ribosome biogenesis and tRNA synthesis (Schmelzle T et al., 2000).

Preferably in the present invention, rapamycin, represented by the following Chemical Formula 1, may be used as an inhibitor of mTOR functioning downstream of the mTOR signaling pathway. Rapamycin, such as that commercially available from Calbiochem, forms a complex with FK-506 binding protein 12 (FKBP12). The interaction of this FKBP12-rapamycin complex with mTOR inhibits the kinase activity of mTOR.

[Chemical Formula 1]

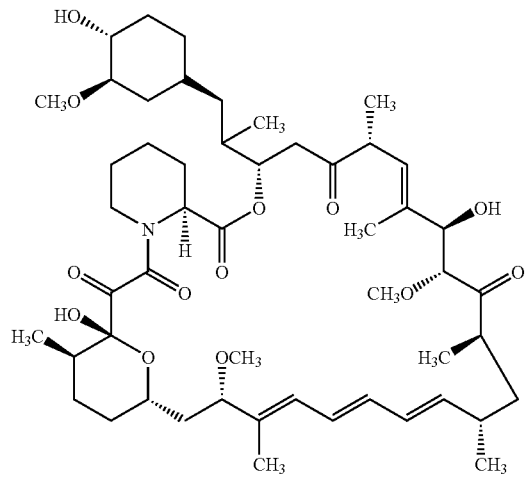

A PI3K inhibitor or an AKT inhibitor can be used as an inhibitor of mTOR functioning upstream of the mTOR signaling pathway. LY294002 (a product from Calbiochem), represented by the following Chemical Formula 2, is a known PIK3 inhibitor. LY294002 inhibits PI3K, but does not inhibit PI4K, an EGR receptor, a PDGF receptor, an insulin receptor, an MAP kinase, an S6 kinase, etc.

[Chemical Formula 2]

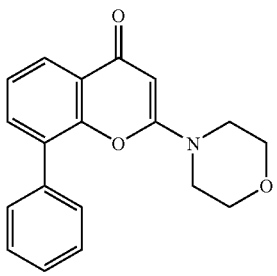

An AKT inhibitor, as an inhibitor of mTOR functioning upstream of the mTOR signaling pathway, may be exemplified by the compound represented by the following Chemical Formula 3, also commercially available from Calbiochem. In the present invention, the expression "AKT inhibitor" is intended to refer to the compound of Chemical Formula 3.

[Chemical Formula 3]

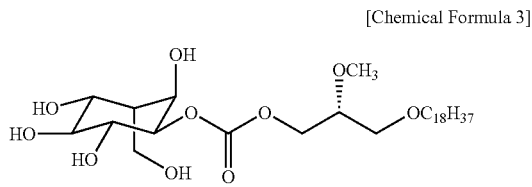

As used herein, the term "human embryonic stem cell" is intended to refer to a cell culture derived in vitro from the inner cell mass of human blastocysts of the fertilized eggs just before nidation, which possesses pluripotency, that is, ability to give rise to any mature cell type, and includes, in a broad sense, embryoid bodies derived therefrom.

The term "osteoblast", as used herein, is intended to refer to a mononucleate cell that is responsible for bone formation. Bone consists of bone matrix and bone cells, which are further divided into osteoblasts and osteoclasts. Bone is a dynamic tissue that is constantly being reshaped by osteoblasts, which build bone, and osteoclasts, which resorb bone. Osteoclasts are a type of bone cell that removes bone tissue by removing the bone's mineralized matrix. Osteoblasts produce a protein mixture known as osteoid, which is composed mainly of Type I collagen. Osteoblasts are also responsible for mineralization of the osteoid matrix with calcium, magnesium, phosphorus, etc.

Advantageous Effects

The composition for inducing stem cells to differentiate into an osteoblastic lineage and the method for differentiating stem cells into an osteoblastic lineage using the composition are useful in the development of cell therapeutics for metabolic bone diseases. Also, the present invention contributes to molecular biological research into the signaling pathway for the differentiation of human embryonic stem cells into an osteoblastic lineage, thus being useful in the discovery of other novel bone-related factors. Providing terminally differentiated mature cells, in addition, the present invention is applied to surgical and pharmaceutical research into metabolic bone diseases. The differentiated cells produced according to the method of the present invention find applications in various medical and pharmaceutical fields, including biological assay systems for medical efficacy using stem cells and assay systems for the medical efficacy of osteogenic inducers and bone tissue enhancements in stem cells.

DESCRIPTION OF DRAWINGS

FIG. 1 is a schematic view illustrating the mechanism of action of rapamycin, LY294002, and an AKT inhibitor in an intracellular signal pathway.

FIG. 2 illustrates a process of inducing human embryonic stem cells to differentiate into osteoblasts in the presence of rapamycin alone or in combination with osteogenic supplements including β-glycerophosphate, dexamethasone and L-ascorbic acid in a schematic view (A), and shows the resulting differentiated cells in optical photographs (B).

FIG. 3 illustrates a process of inducing human embryonic stem cell-derived embryoid bodies to differentiate into osteoblasts by treatment with rapamycin, alone or in combination with osteogenic supplements including β-glycerophosphate, dexamethasone and L-ascorbic acid in a schematic view (A) and shows the resulting differentiated cells in optical photographs (B).

FIG. 4 illustrates a process of dissociating human embryonic stem cell-derived embryoid bodies into single cells and inducing the single cells to differentiate into osteoblasts in the presence of rapamycin alone or in combination with osteogenic supplements including β-glycerophosphate, dexamethasone and L-ascorbic acid in a schematic view (A), and shows the resulting differentiated cells in optical photographs (B).

FIG. 5 is a photograph showing the electrophoresis results of the RT-PCR products using the osteoblast-specific genes obtained from two different human embryonic stem cell lines treated as in FIG. 2.

FIG. 6 is a set of photographs showing the electrophoresis results of RT-PCR products using the osteoblast-specific genes obtained from human embryonic stem cell-derived embryoid bodies treated with rapamycin (R) (A), the PI3K inhibitor LY294002 (LY) (B), and an AKT inhibitor (AKT), along with genes obtained from undifferentiated human embryonic stem cells (ES) and untreated human embryonic stem cell-derived embryoid bodies (C).

FIG. 7 is a chart including two sets of bar graphs showing the relative expression levels of osteoblast-specific genes obtained after the cells of FIG. 3 had differentiated for one week (A) and two weeks (B), as determined by quantitative real-time PCR.

FIG. 8 is a chart including sets of bar graphs showing the relative expression levels of osteoblastic-specific genes obtained after two different human embryonic stem cell lines were treated for three weeks as in FIG. 3, as determined by quantitative real-time PCR.

FIG. 9 is a chart of a set of immunofluorescent photographs showing the differentiated cells of FIG. 3, on which osteoblastic markers BSP and OC were expressed.

FIG. 10 is a chart including a set of immunochemical photographs showing the Alizarin Red S-positive, differentiated cells of FIG. 3.

FIG. 11 is a chart including a set of bar graphs showing the relative expression levels of osteoblastic-specific genes obtained after the human embryonic stem cells of FIG. 3 were treated with osteogenic supplements including β-glycerophosphate, dexamethasone and L-ascorbic acid alone or in combination with rapamycin for two weeks, as determined by quantitative real-time PCR.

FIG. 12 is a chart including a set of immunochemical photographs showing the cells of FIG. 3 after they were differentiated in the presence of osteogenic supplements alone or in combination with rapamycin and stained with Alizarin Red S.

BEST MODE

A better understanding of the present invention may be grasped with reference to the following examples, which are set forth to illustrate, but are not to be construed to limit the present invention.

Example 1

Culture of Human Embryonic Stem Cell

In order to keep them pluripotent, undifferentiated human embryonic stem cells were grown on a feeder layer of mitomycin C-treated mouse embryonic fibroblast (MEF) cells in a DMEM/F12 culture medium (Invitrogen, USA) supplemented with 20% knockout serum replacement (Invitrogen, USA), 0.1 mM non-essential amino acids (NEAA; Invitrogen, USA), 0.1 mM beta-mercaptoethanol, 4 ng/ml recombinant human fibroblast growth factor (FGF) basic (Invitrogen, USA), and 1× penicillin-streptomycin (Invitrogen, USA). One day before culturing human embryonic stem cells, MEF feeder cells maintained in DMEM (Invitrogen, USA) supplemented with 10% fetal bovine serum (Hyclone, USA), 0.1 mM NEAAs, 1× penicillin-streptomycin, and 0.5 mM beta-mercaptoethanol were inactivated for 1.5 hrs with 10 μg/ml mitomycin C (Sigma, USA) and then plated at a density of $7.5 \times 10^4$ cells/cm$^2$ on tissue culture dishes coated with 0.1% gelatin (Sigma, USA). For subcultures, colonies of human embryonic stem cells were triturated into smaller cell clumps using a tool made from a glass Pasteur pipette and the cell clumps were placed at suitable spatial intervals on feeder cells. From two days after the cell clumps were placed on the feed layer, the culture medium was changed with a fresh one with subculturing at intervals of 5 or 6 days.

Example 2

Preparation of Embryoid Bodies and Single Cells from Human Embryonic Stem Cells

In order to prepare consistent sizes of embryoid bodies, human embryonic stem cell colonies were sliced into cell clumps having dimensions of about 500×500 μm using a tool made from a glass pipette, and a suspension of the cell clumps was collected and transferred into bacterial culture dishes. The resulting embryoid bodies were dissociated into single cells by washing with phosphate buffered saline (PBS), adding a 1× trypsin-EDTA solution (TrypLE Express, Invitrogen), incubating at 37° C. for 1~5 min, washing twice with PBS, and plating on Matrigel (BD biosciences, USA)-coated culture dishes.

Example 3

Differentiation of Human Embryonic Stem Cells and Embryoid Bodies into Osteoblasts For osteogenic differentiation by adhesion culturing, the human embryonic stem cells obtained in Example 1, after passage, were cultured in the culture medium of Example 1 for 2 days, and then in a culture medium, free of recombinant human FGF basic, containing 0.1~200 nM rapamycin, 0.01~50 μM LY294002, 0.01~20 μM AKT inhibitor, or conventional osteogenic supplements (10 mM β-glycerophosphate, 0.1 mM Dexamethasone, 0.1 mM L-ascorbic acid) for 7 days, with daily replacement with a fresh embryonic stem cell culture medium (FIG. 2A).

For osteogenic differentiation by embryoid body formation, as shown in FIG. 3A, the human embryonic stem cells obtained in Example 1 were first cultured in the stem cell culture medium of Example 1 for one day after passage, and the stem cell colony was sliced into cell clumps having dimensions of 500×500 μm. After being collected as a suspension, the cell clumps were transferred into bacterial cell culture dishes and incubated for 5 days in a suspension culture manner. Afterwards, the embryoid bodies thus obtained were transferred to Matrigel (BD biosciences, USA)-coated culture dishes, free of human recombinant FGF basic, containing 0.1~200 nM rapamycin, 0.01~50 μM LY294002, 0.01~20 μM AKT inhibitor, or osteogenic supplements (10 mM β-glycerophosphate, 0.1 mM Dexamethasone, and 0.1 mM L-ascorbic acid) for three weeks in an adhesion culture manner to achieve osteogenic differentiation (FIG. 3A).

For osteogenic differentiation by single cell preparation, the human embryonic stem cells obtained in Example 1 were first cultured in the stem cell culture medium of Example 1 for one day after passage, and the stem cell colony was sliced into cell clumps having dimensions of 500×500 μm. After being collected as a suspension, the cell clumps were transferred into bacterial cell culture dishes and incubated for 5 days in a suspension culture manner. The embryoid bodies thus obtained were washed with PBS, treated with 1× trypsin-EDTA (TrypLE Express, Invitrogen) at 37° C. for 1~5 min, washed twice with PBS, and incubated in a suspension culture manner in Matrigel-coated culture dishes, free of recombinant human FGF basic, containing 0.1~200 nM rapamycin, 0.01~50 μM LY294002 and 0.01~20 μM AKT inhibitor, or osteogenic supplements (10 mM β-glycerophosphate, 0.1 mM Dexamethasone, 0.1 mM L-ascorbic acid) (FIG. 4A).

Example 4

Detection of Osteoblastic Marker

<4-1> Reverse Transcriptase PCR (RT-PCR) and Quantitative Real-Time PCR

The differentiation of human embryonic stem cells into osteoblasts in Example 3 was examined by detecting the expression of osteoblast-specific genes through RT-PCR and quantitative real-time PCR. For this, after treatment or non-treatment with rapamycin, LY294002, an AKT inhibitor or osteogenic supplements (10 mM β-glycerophosphate, 0.1 mM Dexamethasone, and 0.1 mM L-ascorbic acid), cells were collected according to differentiation stages and subjected to total RNA isolation using a TRIzol reagent (Invitrogen, USA). The RNA was used as a template to synthesize cDNA with a oligo(dT) primer in the presence of a Superscript II reverse transcriptase, followed by PCR with various primers listed in Table 1, below.

TABLE 1

| Genes | Accession Nos. | | Sequences | Product Size (bp) |
|---|---|---|---|---|
| GAPDH | NM_002046 | Forward | GAAGGTGAAGGTCGGAGTC | 226 |
|  |  | Reverse | GAAGATGGTGATGGGATTTC |  |
| Oct4 | NM_002701 | Forward | GAAGGATGTGGTCCGAGTGT | 243 |
|  |  | Reverse | GTGACAGAGACAGGGGGAAA |  |
| Nanog | NM_024865 | Forward | ACCAGAACTGTGTTCTCTTCCACC | 334 |
|  |  | Reverse | GGTTGCTCCAGGTTGAATTGTTCC |  |

TABLE 1-continued

| Genes | Accession Nos. | | Sequences | Product Size (bp) |
|---|---|---|---|---|
| ALP | NM_000478 | Forward | GGGGGTGGCCGGAAATACAT | 543 |
| | | Reverse | GGGGGCCAGACCAAAGATAG | |
| ALP* | NM_000478 | Forward | CCGTGGCAACTCTATCTTTGG | 70 |
| | | Reverse | GATGGCAGTGAAGGGCTTCTT | |
| α1 type I collagen | NM_000088 | Forward | ATGGATTCCAGTTCGAGTATGGC | 246 |
| | | Reverse | CATCGACAGTGACGCTGTAGG | |
| BMP2 | NM_001200 | Forward | ACCCGCTGTCTTCTAGCGT | 140 |
| | | Reverse | CTCAGGACCTCGTCAGAGGG | |
| BMP4 | NM_130851 | Forward | TGTTCACCGTTTTCTCGACTC | 243 |
| | | Reverse | TCAGGTATCAAACTAGCATGG | |
| BSP | NM_004967 | Forward | CAGTATGACTCATCCGAAG | 280 |
| | | Reverse | CTCCTCTTCTTCTTCATCAC | |
| BSP* | NM_004967 | Forward | AGAGGAAGCAATCACCAAAATGA | 66 |
| | | Reverse | GCACAGGCCATTCCCAAA | |
| Cbfa1 | NM_004348 | Forward | CGGCAAAATGAGCGACGTG | 268 |
| | | Reverse | CACCGAGCACAGGAAGTTG | |
| Osteocalcin | NM_199173 | Forward | CACTCCTCGCCCTATTGGC | 138 |
| | | Reverse | GCCTGGGTCTCTTCACTACCT | |
| Osteonectin | NM_003118 | Forward | AGCACCCCATTGACGGGTA | 105 |
| | | Reverse | GGTCACAGGTCTCGAAAAGC | |
| Osteopontin | NM_000582 | Forward | ACTCGAACGACTCTGATGATGT | 224 |
| | | Reverse | GTCAGGTCTGCGAAACTTCTTA | |
| Osteo-protegerin | NM_002546 | Forward | AGCACCCTGTAGAAAACACAC | 195 |
| | | Reverse | ACACTAAGCCAGTTAGGCGTAA | |
| Osterix | NM_152860 | Forward | CCCAGGCAACACTCCTACTC | 175 |
| | | Reverse | GGCTGGATTAAGGGGAGCAAA | |
| Osterix* | NM_152860 | Forward | GCTCTGCTCCAAGCGCTTTA | 55 |
| | | Reverse | GGTGCGCTGGTGTTTGCT | |

PCR results for the expression of osteoblast-specific genes of Example 3, as seen in FIG. 5, indicate that the osteoblastic markers Cbfa-1, osteocalcin, and osteoprotegerin are expressed in each of two independently established cell lines cultured in the presence of rapamycin in an adhesion culture manner. Also, osterix, BMP2, and osteonectin genes were observed to be expressed in both cell lines, but in different patterns. The genes were expressed at greater levels in the presence of 20 nM than 10 nM of rapamycin. In addition, sensitivity to the expression of osteoblast-specific genes, although varying with cell lines, was observed to show the same overall direction. It is accordingly understood that the efficient induction of human embryonic stem cells into osteogenic differentiation requires the addition of rapamycin in an amount that is sufficient to induce differentiation but not so high as to induce cytotoxicity.

With reference to FIG. 6, the expression of osteoblast-specific genes was observed to differ in amount and type among the osteoblasts differentiated from embryoid bodies in the presence of rapamycin, LY294002 or an AKT inhibitor. When differentiated in the presence of rapamycin, the osteoblasts expressed marker genes at the highest diversity (BMP2, osteocalcin, Cbfa-2, osterix, osteoprotegerin, GATA2, CMP) and in amounts as great as or greater than when differentiated in the presence of LY294002 or an AKT inhibitor. Of the osteoblast-specific genes, osterix and osteoprotegerin were both expressed at high levels in the osteoblasts differentiated in the presence of the three compounds.

As to the expression pattern of osteoblast-specific genes, it can be analyzed by quantitative real-time PCR. As seen in FIG. 7, when differentiation was induced in the embryoid bodies for one week, the expression of osteoblast-specific genes was increased 3.24-fold for Cbfa1, 1.38-fold for BMP2, 6.54-fold for BSP, 1.84-fold for osteocalcin, and 2.89-fold for osteopontin in a rapamycin-specific manner. After two weeks of differentiation culture, the expression level was increased 2.11-fold for Cbfa-1, 1.59-fold for osterix, 1.34-fold for BMP2, 1.18-fold for BMP4, 1.63-fold for BSP, 1.35-fold for α1 type I collagen, 1.61-fold for osteocalcin, 2.18-fold for osteoprotegerin, 1.94-fold for osteonectin, and 5.81-fold for osteopontin in the presence of rapamycin (FIG. 7). Also, it was observed that osterix, BMP2, BMP4, α1 type I collagen, osteocalcin, osteoprotegerin, osteonectin, and osteopontin continued to increase in expression level even after three weeks of differentiation culture (FIG. 8). In response to rapamycin, both of the human embryonic stem cell lines were similarly increased in the expression levels of osterix, BMP4, α1 type I collagen, osteoprotegerin, and osteopontin, but decreased in the expression level of Cbfa1 after three weeks of differentiation culture. As for BMP2, BSP, osteocalcin and osteonectin, however, their expression levels were measured to differ from one cell line to the other.

Referring to FIG. 11, the expression of osteoblast-specific genes in the cells differentiated in the presence of conventional osteogenic supplements (10 mM β-glycerophosphate, 0.1 mM Dexamethasone, 0.1 mM L-ascorbic acid) alone or in combination with rapamycin was quantitatively analyzed. After one week of differentiation culture with the osteogenic supplements, the expression level was increased 4.54-fold for Cbfa1, 2.22-fold for osterix, 2.21-fold for BMP2, 1.93-fold for BMP4, 2.62-fold for BSP, and 2.91-fold for osteoprotegerin. On the other hand, differentiation induction with the osteogenic supplements in combination with rapamycin resulted in an increase in the expression level not only of Cbfa1 by 2.27 times, osterix by 2.22 times, BMP2 by 2.21 times, BMP4 by 1.93 times, BSP by 2.62 times, and osteoprotegerin by 2.91 times, but also of α1 type I collagen by 1.82 times, osteocalcin by 3.36 times, and osteoprotegerin by 2.91 times, neither of which showed response to the osteogenic supplements.

<4-2> Analysis for Mineralization by Alizarin-Red S Staining

The cells obtained using the three differentiation inducing techniques described in Example 3 were analyzed for mineralization using an Alizarin-Red S staining method. After aspirating the culture medium, the cells on the culture dish were washed with PBS and fixed at 4° C. for 1 hr with 70% ethanol. Thereafter, the cells were stained with a 40 mM alizarin red (AR) solution (pH 4.2) for 10 min, washed with distilled water, and observed for mineral nodule formation under an optical microscope before they were completely dried. As seen in FIG. 10, the cells which were induced to differentiate by rapamycin were positively stained with Alizarin-Red. When cultured in the co-presence of conventional osteogenic supplements (10 mM β-glycerophosphate, 0.1 mM Dexamethasone, 0.1 mM L-ascorbic acid) and rapamycin, a relatively higher number of the cells were stained with Alizarin Red (FIG. 12). A culture period of three weeks was required to maximize the number of Alizarin Red-positive cells upon osteogenic differentiation with rapamycin alone. The co-presence of osteogenic supplements (10 mM 3-glycerophosphate, 0.1 mM Dexamethasone, 0.1 mM L-ascorbic acid) and rapamycin allowed the cells to be visualized with Alizarin Red S in an earlier time.

<4-3> Immunofluorescent Staining

The osteogenic differentiation of the cells obtained using the three differentiation inducing techniques described in Example was identified by immunofluorescent staining. First, the cells were placed on a 1 cm$^2$ cover glass and the medium was aspirated. Following washing with PBS, the cells were incubated with a fixing solution (citrate-acetone-formaldehyde) for about 30 sec at room temperature and washed with distilled water for 45 sec. Next, treatment with 3% bovine serum albumin/phosphate buffered saline (BSA/PBS) for 30 min was followed by incubation with a primary antibody for 12 hrs. Then, the cells were washed three times for 15 min in 0.1% Triton X-100/PBS before labeling by incubation with an Alexa488-conjugated secondary antibody (Molecular probes, USA) for 30 min at room temperature. The cells were washed again three times in 0.1% Triton X-100/PBS for 15 min each time for observation under a fluorescent microscope (Olympus, Japan). In order to identify osteogenic differentiation, anti-bone sialoprotein (anti-BSP, Chemicon; 1:100), and anti-osteocalcin (R&D Systems; 1:500) were used for immunofluorescence. As seen in FIG. 9, visualization with an antibody against the late osteoblastic marker bone sialoprotein (BSP) or osteocalcin showed that when induced by rapamycin, the embryonic stem cells were differentiated into osteoblasts in the same or greater number than when induced by the conventional osteogenic supplements. Accordingly, it is understood that rapamycin is as good as or better than the conventional osteogenic supplements in terms of its ability to induce osteogenic differentiation.

MODE FOR INVENTION

In an embodiment of the present invention, as shown in FIG. 1, human embryonic stem cells (FIG. 2) or embryoid bodies (FIGS. 3 and 4) derived from human embryonic stem cells were induced to differentiate into an osteoblastic lineage in the presence of rapamycin, LY294002 or an AKT inhibitor, which is known to inhibit a downstream signaling molecule in the PI3K signaling pathway and thus play a critical role in controlling the proliferation of human embryonic stem cells. The osteogenic differentiation, as seen in FIGS. 5 to 8, was identified as quantitatively analyzed for the expression of osteoblast-specific genes by RT-PCR. Osteoblastic markers were found to increase in expression level when human embryonic stem cells were cultured in culture media containing 10 mM LY294002, 0.1 mM AKT inhibitor, or 20 nM rapamycin for 5 days, as illustrated in Stage II of FIG. 2, or when embryoid bodies derived from human embryonic stem cells were cultured in culture media containing 10 mM LY294002, 0.1 mM AKT inhibitor, or 20 nM rapamycin for three weeks, as illustrated in Stage II of FIG. 3, indicating that these three compounds have the ability to induce osteogenic differentiation. Of the compounds, rapamycin was observed to have the most potent induction activity, even at low doses (FIG. 6). After embryoid bodies derived from human embryonic stem cells were cultured for three weeks in the presence of 20 nM rapamycin, as illustrated in Stage II of FIG. 3, the cells were positively stained with both Alizarin Red S, which is specific for calcium phosphate-deposited osteoblasts (FIG. 10), and immunofluorescent dye with antibodies to the later osteoblastic makers BSP and osteocalcin, indicating that rapamycin is able to induce embryoid bodies to differentiate into mature osteoblasts.

In a concrete embodiment of the present invention, osteogenic differentiation was assayed when human embryonic stem cells were cultured: 1. in the presence of rapamycin, known as an mTOR inhibitor, only; 2. in the presence of conventional osteogenic supplements (β-glycerophosphate, Dexamethasone, and L-ascorbic acid), known to effectively induce osteogenic differentiation; and 3. in the co-presence of rapamycin and osteogenic supplements (β-glycerophosphate, Dexamethasone, L-ascorbic acid). Although it is a single chemical, rapamycin showed osteogenic differentiation activity as good as or better than that of the conventional osteogenic supplements in terms of cell morphology (FIG. 2) and the expression level of osteoblastic markers (FIGS. 7 and 8). The most efficient differentiation into mature osteoblasts was detected when embryoid bodies derived from human embryonic stem cells were treated with 20 nM rapamycin for three weeks, as illustrated in Stage II of FIG. 3. When using osteogenic supplements (β-glycerophosphate, Dexamethasone, and L-ascorbic acid) and rapamycin in combination, a culture period of two weeks was sufficient to express osteoblastic markers (FIG. 11) and induce differentiation into mature osteoblasts (FIG. 12).

Meanwhile, as seen in FIG. 3, embryoid bodies were prepared from human embryonic stem cells and induced to differentiate into osteoblasts. In this regard, first, human embryonic stem cells were grown to colonies in a fresh culture medium which was replaced 48 hrs after passage, and the colonies were sliced into cell clumps having dimensions of about 500×500 μm. These cell clumps were cultured in a suspension culture manner to form embryoid bodies which were then incubated with LY294002 (0-50 μM), an AKT inhibitor (0-20 μM), or rapamycin (0-200 nM) for 1~3 weeks. Compared to a control, which was not treated with the inhibitors, the embryoid bodies treated with the inhibitors were found to increase in the expression level of osteoblast-specific genes (FIGS. 5 to 8). In both cases, in which embryoid bodies derived from human embryonic stem cells were attached to culture dishes, as schematically illustrated in FIG. 3A, and in which single cells dissociated from the embryoid bodies were attached to culture dishes, as schematically illustrated in FIG. 4A, it was observed that osteogenic differentiation took place efficiently. The single cell dissociation is expectedly useful in the quantitative and qualitative analysis for properties of differentiated cells.

In accordance with an aspect of the present invention, a composition for inducing the osteogenic differentiation of human embryonic stem cells may be preferably provided as a medium composition. The medium composition may comprise an inhibitor of mTOR, that is, rapamycin, LY294002, and/or an AKT inhibitor in addition to basic additives or conventional osteogenic supplements. The basic additives include sera, amino acids, antibiotics, differentiation-inhibiting factors, etc. Rapamycin is known as an immunosuppressive, like FK506 and cyclosporine. Hence, FK506 and cyclosporine are also contained in the composition for inducing the osteogenic differentiation of human embryonic stem cells.

The medium composition in accordance with the present invention preferably contains an mTOR inhibitor, for example, LY294002, at a concentration from 0.1 to 50 μM, an AKT inhibitor at a concentration from 0.1 to 20 μM, or rapamycin at a concentration from 0.1 to 200 nM. More preferably, the concentration of the mTOR inhibitor ranges from 0.1 to 20 μM for LY294002, from 0.1 to 10 μM for an AKT inhibitor or from 0.1 to 100 nM for rapamycin.

In accordance with another aspect thereof, the present invention provides a method for the osteogenic differentiation of human embryonic stem cells using the composition containing the mTOR inhibitor.

In the present invention, the osteogenic differentiation can be achieved using an adhesion culture method, an embryoid body formation method, or a single cell dissociation method. The adhesion culture method is directed to the differentiation of human embryonic stem cells while they are attached to culture dishes. In the embryoid body formation method, embryoid bodies are derived from stem cells one day after passage, and are induced to differentiate into osteoblasts. As for the single cell dissociation method, embryoid bodies are also formed as in the embryoid body formation method and on day 4 after the formation, the embryoid bodies are dissociated into single cells which are then cultured in the adhesion culture manner.

First, a description is given of the adhesion culture method. As seen in FIG. 2A, human embryonic stem cells are co-cultured with mitomycin C-treated MEF (mouse embryonic fibroblast) feeder cells in a nutrient DMEM/F12 medium (Invitrogen, USA) containing 20% knockout serum replacement (Invitrogen, USA), 0.1 mM non-essential amino acids (NEAA; Invitrogen, USA), 0.1 mM beta-mercaptoethanol, 4 ng/ml recombinant human FGF basic (Invitrogen, USA), and 1× penicillin-streptomycin (Invitrogen, USA) for two days (Stage I). Afterwards, the human embryonic stem cells are induced to differentiate into osteoblasts by being cultured for five days in a medium that is the same except that it is free of recombinant human FGF basic and is supplemented with LY294002, an AKT inhibitor, rapamycin, and/or conventional osteogenic supplements (10 mM 3-glycerophosphate, 0.1 mM Dexamethasone, and 0.1 mM L-ascorbic acid) (Stage II).

Osteogenic differentiation using the embryoid body formation method is schematically illustrated in FIG. 3A. Initially, human embryonic stem cells are cultured for one day in the same manner as in the adhesion culture method, after which the colonies thus grown are sliced into cell clumps using a tool made from a glass pipette. The cell clumps are cultured for four days in a culture medium (80% knockout DMEM, 20% fetal bovine serum, 1 mM L-glutamine, 0.1 mM β-mercaptoethanol, 1 mM non-essential amino acids) to form embryoid bodies (Stage I), followed by culturing the embryoid bodies for an additional three weeks in the presence of LY294002, an AKT inhibitor, rapamycin, and/or osteogenic supplements (10 mM β-glycerophosphate, 0.1 mM Dexamethasone, and 0.1 mM L-ascorbic acid) to induce osteogenic differentiation (Stage II).

Turning to FIG. 3A, osteogenic differentiation by single cell dissociation is schematically illustrated. As in the adhesion culture method and the embryoid body formation method, embryoid bodies are prepared one day after the passage of human embryonic stem cells and are cultured for four days in the embryoid body culture medium (Stage I). On day 4 after culturing, the embryoid bodies are dissociated into single cells using a trypsin-EDTA solution (TrypLE Express, Invitrogen), followed by adhesion culturing for an additional three weeks in the same medium in the presence of LY294002, an AKT inhibitor, rapamycin, and/or osteogenic supplements (10 mM β-glycerophosphate, 0.1 mM Dexamethasone, 0.1 mM L-ascorbic acid) (Stage II).

The osteogenic differentiation of human embryonic stem cells by the three differentiation methods can be monitored using reverse transcriptase PCR (RT PCR), quantitative real-time PCR, immunofluorescent staining, and Alizarin Red S staining.

As seen in the photograph of FIG. 5, taken of the gel on which RT-PCR products were electrophoresed, when differentiated with rapamycin, two independently established cell lines were found to express distinctively higher levels of the osteoblastic markers Cbfa-1, Osteocalcin and Osteoprotegerin at higher levels, compared to an undifferentiated control. The expression levels of Osteocalcin and Osteonectin were higher at a dose of 20 nM than 10 nM. Hence, when 20 nM of rapamycin was added to a culture medium, the osteoblast-specific genes were most effectively expressed, with no cytotoxic effects occurring.

Referring to FIG. 6, the cells differentiated by the embryoid body formation method illustrated in FIG. 3A were assayed for osteogenic differentiation through RT-PCR for osteoblast-specific genes. As seen in FIG. 6, LY294002, an AKT inhibitor, and rapamycin were all observed to increase the expression levels of osteoblast-specific genes. Above and beyond the LY294002 and AKT inhibitor, rapamycin was found to more effectively induce embryoid bodies to differentiate into osteoblasts, as qualitatively and quantitatively analyzed using osteoblastic markers (BMP2, Osteocalcin, Cbfa-2, Sterix, Osteoprotegerin, GATA2, CMP). These results therefore indicate that the down-regulation of the mTOR signaling pathway (that is, inhibiting mediators downstream of mTOR) rather than the up-regulation (that is, inhibiting mediators upstream of mTOR, such as PI3K or AKT) is more effective in the induction of osteogenic differentiation.

The ability of rapamycin to induce osteogenic differentiation was also confirmed using molecular biological methods, such as quantitative real-time PCR)(FIG. 7) and immunofluorescent staining (FIG. 10), and Alizarin Red S staining, specific for osteoblasts. After one week of incubation of embryoid bodies with rapamycin, as illustrated in FIG. 3A, osteoblastic markers were observed to increase in expression level (FIG. 7), but it took an additional three weeks of incubation with rapamycin to obtain a mature osteoblast phenotype.

Finally, the cells differentiated using a single cell dissociation method, in which embryoid bodies are formed from human embryonic stem cells and dissociated into single cells, are assayed for osteogenic differentiation as measured by quantitative real-time PCR (FIG. 8) and immunofluorescent staining (FIG. 11).

In order to induce osteogenic differentiation, rapamycin, LY294002, and an AKT inhibitor were used at various concentrations in culture media. It was observed that osteoblast-specific genes were efficiently expressed in the presence of 10 µM of LY29400, 1 µM of an AKT inhibitor, or 220 nM of rapamycin without the occurrence of cytotoxicity. The cells derived from human embryonic stem cells in this way are osteoblast progenitor cells which can be grown to produce osteoblasts in large quantities.

When cultured in the medium composition comprising an mTOR inhibitor, for example, LY294002, at a concentration ranging from 0.1 to 50 µM, an AKT inhibitor at a concentration from 0.1 to 20 µM, or rapamycin at a concentration from 0.1 to 200 nM, human embryonic stem cells can be induced to differentiate into osteoblasts. More preferably, the concentration of the mTOR inhibitor ranges from 0.1 to 20 µM for LY294002, from 0.1 to 10 µM for an AKT inhibitor, or from 0.1 to 100 nM for rapamycin.

INDUSTRIAL APPLICABILITY

Osteoblasts differentiated from human embryonic stem cells in accordance with the method of the present invention can be used for cell therapy for bone-related diseases.

The invention claimed is:

1. A method for differentiating human embryonic stem cells or embryoid bodies derived from human embryonic stem cells into osteoblasts comprising culturing the human embryonic stem cells in a culture medium containing an mTOR inhibitor or an mTOR signaling pathway inhibitor, and an osteogenic supplement selected from the group consisting of β-glycerophosphate, dexamethasone, L-ascorbic acid, and combinations thereof, wherein the mTOR inhibitor or the mTOR signaling pathway inhibitor is selected from the group consisting of rapamycin, as depicted in Chemical Formula 1, a PI3K inhibitor, as depicted in Chemical Formula 2, and an AKT inhibitor, as depicted in Chemical Formula 3:

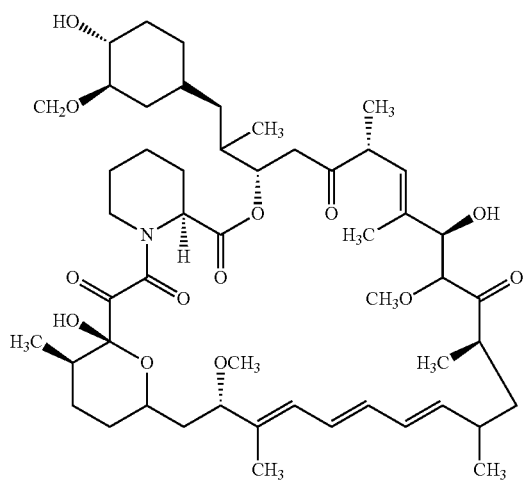

[Chemical Formula 1]

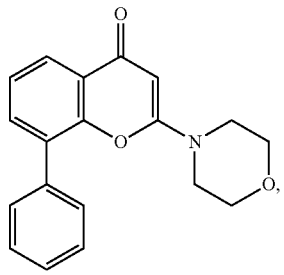

[Chemical Formula 2]

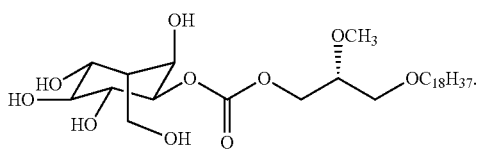

[Chemical Formula 3]

2. The method according to claim 1, wherein the rapamycin is at a concentration of 0.1~100 nM in the culture medium.

3. The method according to claim 1, wherein the compound of Chemical Formula 2 is at a concentration of 0.1~20 μM in the culture medium.

4. The method according to claim 1 wherein the compound of Chemical Formula 3 is at a concentration of 0.1~10 μM in the culture medium.

5. The method according to any one of claims 1 or 2-4, wherein the embryoid bodies derived from human embryonic stem cells include embryonic stem cell clumps having a size of 500×500 μm.

6. The method according to any one of claims 1 or 2-4, wherein the embryoid bodies derived from human embryonic stem cells are dissociated into single cells.

7. A composition for inducing human embryonic stem cells or embryoid bodies derived from human embryonic stem cells to differentiate into osteoblasts, comprising at least one of the compounds as depicted in Chemical Formulas 1 to 3, and an osteogenic supplement selected from the group consisting of β-glycerophosphate, dexamethasone, L-ascorbic acid, and combinations thereof:

[Chemical Formula 1]

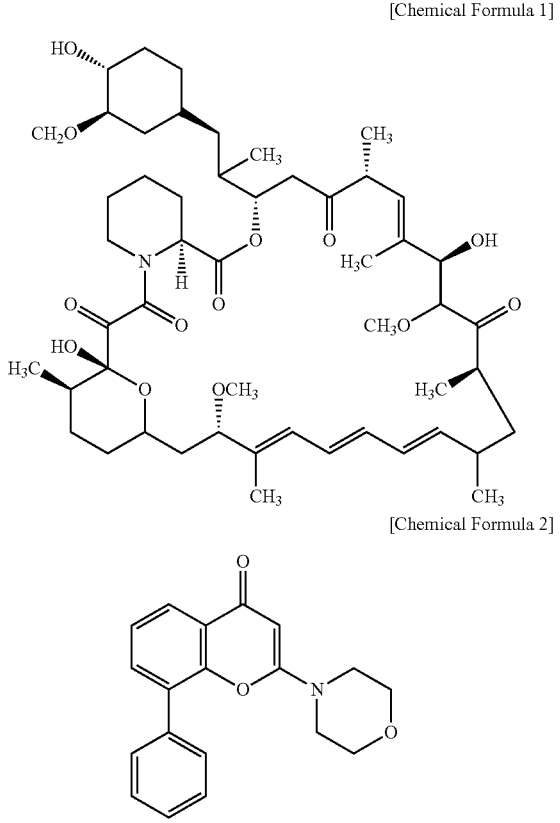

[Chemical Formula 2]

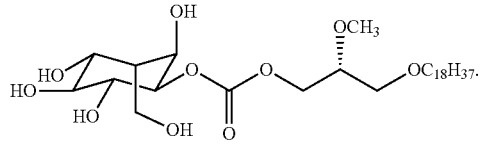

[Chemical Formula 3]

8. A culture medium composition for inducing human embryonic stem cells or embryoid bodies derived from human embryonic stem cells to differentiate into osteoblasts, comprising the compound of Chemical Formula 1 at a concentration of 0.1~100 nM, the compound of Chemical Formula 2 at a concentration of 0.1~20 uM, the compound of Chemical Formula 3 at a concentration of 0.1~10 uM, or a combination thereof, wherein Chemical Formulas 1 to 3 are as depicted in claim 7, and an osteogenic supplement selected from the group consisting of β-glycerophosphate, dexamethasone, L-ascorbic acid, and combinations thereof.

9. The culture medium composition according to claim 8, comprising the compound of Chemical Formula 1 at a concentration of 0.1~20 nM wherein Chemical Formula 1 is as depicted in claim 7.

10. The culture medium composition according to claim 8, comprising the compound of Chemical Formula 2 at a concentration of 0.1~10 μM wherein Chemical Formula 2 is as depicted in claim 7.

11. The composition according to claim 8, comprising the compound of Chemical Formula 3 at a concentration of 0.1~5 μM wherein Chemical Formula 3 is as depicted in claim 7.

12. The composition according to one of claims 8 to 11, wherein the β-glycerophosphate is at a concentration of 10 mM, wherein the dexamethasone is at a concentration of 0.1 mM, and wherein the L-ascorbic acid is at a concentration of 0.1 mM.

* * * * *